United States Patent [19]
Neefe

[11] Patent Number: 4,592,752
[45] Date of Patent: Jun. 3, 1986

[54] NON-OPTICAL CORNEAL DRUG DELIVERY

[76] Inventor: Charles W. Neefe, 811 Scurry St., Box 429, Big Spring, Tex. 79720

[21] Appl. No.: 762,147

[22] Filed: Aug. 2, 1985

[51] Int. Cl.⁴ .............................................. A61K 9/22
[52] U.S. Cl. .................................................. 604/895
[58] Field of Search ........................ 604/893, 894, 895

[56] References Cited

U.S. PATENT DOCUMENTS 4,484,922  3/1984  Rosenwald ......................... 604/895

FOREIGN PATENT DOCUMENTS 1003914  11/1977  Fed. Rep. of Germany ...... 604/895

Primary Examiner—John D. Yasko

[57] ABSTRACT

A corneal drug delivery device that releases a drug contained in the corneal drug delivery device at a predetermined rate. The drug delivery device has an opening or aperture in the center substantially the size of the pupil and a diameter and curvature substantially the same as the cornea. The convex surface of the device is tapered to form a thin flexible inner edge around the central pupil aperture. The outer peripheral edge is also thin and flexible to allow the device to assume the shape of the cornea upon which it is placed.

25 Claims, 4 Drawing Figures

NON-OPTICAL CORNEAL DRUG DELIVERY

The desire to change and enhance the apparent color of the eye was recorded by the Egyptians five thousand years ago. Cosmetic makeup for the eye area accounts for the larger percentage of the cosmetic sales.

PRIOR ART

Several contact lenses have been produced in an effort to achieve cosmetic eye color change.

One attempt employed a laminated structure with a painted opaque plastic member. The result was a thick heavy lens which was difficult to fabricate and difficult to wear. A later attempt employed a colored opaque porous member surrounding a clear cylinder from which the lens was cut by lathing. This resulted in a lens having a pupil and iris pattern and the porous member had tendencies to flake and chip at the edge. (U.S. Pat. No. 3,454,332—Siegel). A third generation of colored lenses provided a thin layer of colored opaque markings placed in a clear material. The opaque colored marking radiated from the center of the clear material in a geometric pattern.

Neefe U.S. Pat. Nos. 3,710,796, 3,760,807, 3,786,812, 3,957,049 describe methods of corneal drug delivery using corrective contact lenses.

SUBJECT OF THE INVENTION

The delivery of drugs to the cornea at the desired levels over an extended period of time has been a difficult task. This is due in part to the fact that the cornea has no blood supply, and therefore the circulatory system cannot be relied upon to transport the medications to the cornea. This renders continuous intravenous drip, suppositories, injections and oral administration of drugs of little practical value for delivering medications to the corneal tissues. The use of these delivery methods will in most cases result in a toxic level of the drug in the body fluids beyond the acceptance of the active centers before the effective dosage is reached in the corneal tissue.

Moreover, drops or liquid forms of medication instilled in the eye are quickly diluted by the tears and are rapidly carried away by accelerated lacrimation. The administration of medication orally is unpredictable, as the food and fluid intake of the patient before and after administration can dilute, concentrate or eliminate the medications at greatly varying rates. Further, injections produce large dosages immediately followed by a steady decrease in the availability level of medication.

The medication is contained in the peripheral segment and is released at a predetermined rate directly to the epithelium of the cornea. As the drug is absorbed into the ocular tissue, the drug will be available at a constant predetermined level.

The release rate of the drug to the corneal tissue is controllable by many methods. Examples:
1. The solubility of the drug in water,
2. The water content of the lens material,
3. The permeability of the lens material,
4. Microencapsulation of the drug within the lens,
5. Pre-extraction of the lens,
6. Barriers to retard drug migration from the lens,
7. Dispursed within a parsimonious particle to form a matrix.

The release rate of the drug from the peripheral zone may be controlled by a variety of techniques. For example, control of the release rate of the drug may be controlled by varying the solubility of the drug in water, by control of the water content of the material or by the permeability of the material. Rate of release of the drug may also be provided by microencapsulation of the drug within the device, or by pre-extraction. Control of release rate may also be provided with the use of barriers to retard drug migration, or the drug may alternately be dispersed within a parsimonious particle to form a matrix in the lens.

The most effective and useful method of controlling release rate is the use of receptor polymer particles containing the drug within the particles. The drug containing particles are then dispersed within a matrix of drug transporting material within the peripheral zone. The receptor polymer has a low water content and may comprise: vinylpyrrolidone 10% to 50% methyl methacrylate 10% to 40%, ethyleneglycol monomethacrylate 20% to 40%. Cross-linking agents such as allyl methacrylate and ethylene dimethacrylate may be used from 0.1% to 5% to slow the release rate further. An increase in the amount of vinylpyrrolidone also slows the release rate from the particle. Increasing the amount of ethyleneglycol monomethacrylate will increase the rate of drug release from the particle. An example of a drug transporting material suitable for use with the invention is ethyleneglycol monomethacrylate cross-linked with 0.2% ethyleneglycol dimethacrylate when polymerized such that hydrated water soluble drugs may migrate freely through the material. This method of drug delivery is excellent for the administration of pilocarpine oil or pilocarpine hydrochloride, since a very slow delivery rate is desired over an extended period of time for the control of glaucoma.

Antimicrobial drugs will require a faster release rate, but for a shorter period of time. Examples of useful antimicrobial agents are tetracycline, sulfonamides, ampicillin trihydrate, oxytetracycline, penicillin, chloramphenicol, nystatin and many others. It is understood that each drug may require a different release rate and duration to obtain the desired therapeutic effect.

Another example of a receptor particle and supporting matrix comprises 0.10 grams of pilocarpine oil mixed by ultrasonic energy with 30 grams vinylpyrrolidone, 20 grams of methyl methacrylate, 48 grams of ethyleneglycol monomethacrylate, 2 grams of ethylene dimethacrylate, and 0.3 grams of tertiary butyl peroctoate. The mixture is placed in an oven at 70° C. under a nitrogen atmosphere for five hours to effect polymerization. The resultant friable mass is then reduced to a powder.

The solid receptor particles are dispersed in a partially polymerized liquid comprising 100 grams of ethyleneglycol monomethacrylate, 0.2 grams of ethyleneglycol dimethacrylate and 0.3 grams of tertiary butyl peroctoate. The above mixture is polymerized in a nitrogen atmosphere by heating to 70° C. for 5 hours to form the drug transporting matrix.

An important aspect of the invention is that material containing receptor particles made by the above method may be recharged or reactivated after use by immersing the material in a concentrated solution of pilocarpine hydrochloride for eight hours. The use of ultra-sonic energy will increase the absorption of the drug. The desired therapeutic effect can then again be obtained from the recharged device. The recharged receptor particles retain and slowly release the drug due to the affinity of the receptor particles for the drug molecules when in solution.

The ability to recycle or replenish the medication is of economic importance for many chronic disorders such as glaucoma and diabetes. A drug receptor may be any substance which has an affinity for the drug and concentrates the drug. This ability to recycle is based on a reversible bond between the medication and the receptor material. The effectivity of all drugs depend upon a bond with the biopolymer concerned. The drug delivery bonds are reversible, that is the bond may be easily cleaved. Examples of reversible bonds are ionic, polor, hydrogen, hydrophobic and the von der Waals forces. Covalent bonds in which an electron is shared are irreversible and are not suitable for drug delivery.

The selective bonding of a drug is accomplished by providing receptor sites having moieties of topography which mirror the active sites of the drug molecular topography. The close proximity of the atomic surfaces gives rise to the reversible bonds much as von der Walls forces, hydrogen bond and hydrophobic bonds which provide the means of drug delivery. Since the receptors required may be insoluble in the carrier or may be rendered inactive by the carrier monomers during polymerization the use of a particle containing the receptor in a matrix of drug transporting material is desirable. The particles also provide a large surface area as they may be finely divided and evenly distributed throughout the carrier material.

A detailed description of the drug and receptor active sites and the molecular forces may be found in Andrejus Korolkovas' book, "Essentials of Molecular Pharmocology", copyright 1970 by John Wiley & Sons, Inc.

The selective bonding and affinity for the drug in solution results in a concentration of the drug in the receptor media. This affinity may be with the hydrophilic material itself or a receptor embedded within a hydrophilic carrier. The selective bonding and concentration of the drug from the storage solution provides for drug economy and control of release action.

A hydrophilic material composed of diacetone acrylamide 30 percent, methyl methacrylate 20 percent, ethyleneglycol monomethacrylate 49 percent, ethylene dimethacrylate 1 percent when polymerized and hydrated will contain less than 20 percent water when fully hydrated. Pilocarpine will diffuse slower from the polymer containing less water and meter the flow of drug to the cornea.

Present drug delivery contact lenses are intended for persons requiring visual refractive correction to obtain good visual acuity. The drug delivery lenses are medical devices for visual correction and are not intended for use by the large percentage of the population who do not need or want visual correction.

Delivery of medications to the eye does not require a visual refractive correction. One single aperture device will fit all cornea curvatures.

The manufacture of plano or zero power contact lenses is most difficult and expensive. A solution has been found by an ocular device with central visual aperture. The visual aperture being from 4.0 milimeters to 7.0 milimeters in diameter surrounded by a circular hydrogel material. The edges of the central aperture are tapered on the convex surface thereby thinning the device around the aperture. This thinning of the aperture edge is necessary to prevent the tear miniscus formed by surface tension at the aperture edge. The edge thinning also provides a comfortable device and minimum of foreign body sensation as the eyelid travels over the aperture during the blink.

The opening at the center to the atmosphere prevents hypoxia and the formation of corneal edema. The non-refraction open aperture device can be tolerated for extended periods of time without the edema problems encountered with refractive lenses. The materials used are stronger and more durable since no consideration of oxygen permeability is required. The aperture device may be tinted by dying or by adding colorant to the liquid monomer before polymerization. The aperture non-refractive device is made from any of the available soft lens materials. Materials which are translucent are useful as the central visual area is in an open aperture. The material surrounding the central hole must provide comfort and the desired drug release qualities.

EXAMPLES OF THE COLORANTS

FD and C Green #6, Leeben Color Blue LA-589, Brown LS-595, Green 16128 and Violet LS-611.

The acid dyes, known as azo dyes, containing nitrogen to nitrogen bonds —N=N— may be used to practice the invention as may the dyes known as reactive dyes and the sulphur dyes. The sulphur dyes are fixed or made fast by removing the sodium sulphide which made the dye soluble. Reactive dyes require no special fixing step, only extraction on unreacted dye, as they react chemically with the material and are thus made permanent. The properties of dyes are well known to the art.

| EXAMPLES OF THE MONOMER MIXTURE: | |
|---|---|
| (1) Ethylene glycol monomethacrylate | 64.8% |
| Diethylene glycol monomethacrylate | 7.056% |
| Ethylene glycol dimethacrylate | 0.144% |
| Water | 20.9% |
| Ammonium Persulfate | 1.1% |
| 2-dimethylaminoethyl acetate | 6.0% |
| (2) Ethylene glycol monomethacrylate | 54.7% |
| Diethylene glycol monomethacrylate | 17.2% |
| Diethylene glycol dimethacrylate | 0.6% |
| Ammonium Persulfate | 1.1% |
| Dimethylaminoethyl acetate | 5.8% |

Low water content hydrophilic materials having a water content of 25 to 40 percent water by weight have provided consistently fine results. Low water devices are strong, durable and they resist tearing.

It has been discovered that the conventional fitting techniques used for soft corrective contact lenses cannot be used with the aperture drug release devices. The same hydrophilic materials may be used however the fitting philosophy cannot be used.

In order to center around the pupil the aperture drug release device must have a shorter concave radius of curvature. Soft refractive contact lenses are fitted having a concave radius longer than the convex radius of the cornea. The corrective soft contact lenses are also fitted with a diameter larger than the cornea. If these parameters are used for the aperture device, the device will not center around the pupil. The soft aperture drug release device is made having a diameter larger or smaller than the cornea. In fitting the aperture device a diameter of from 10.0 milimeters to 16.0 milimeters has been found useful with a concave radius from 1.20 milimeter longer to 1.60 milimeters shorter than the cornea.

A corneal curvature of 48.00 diopters has a convex radius of 7.03 milimeters. An aperture cosmetic device having a minimum concave radius of 5.43 milimeters could be used.

A corneal curvature of 39.00 diopters has a convex radius of 8.65 milimeters therefore an aperture cosmetic device having a maximum concave radius of 9.85 could be used. The useful concave radii ranges from 5.43 milimeters to 9.85 milimeters.

Figure 1:
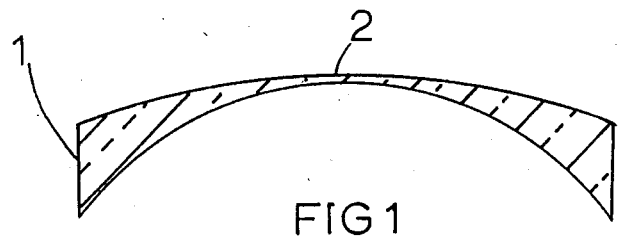
FIG. 1 shows a negative refractive lens in section.

The device functions as follows:

Negative refractive power soft contact lenses FIG. 1 have a thin flexible center 2 FIG. 1 and a thick less flexible edge 1 FIG. 1.

Figure 2:
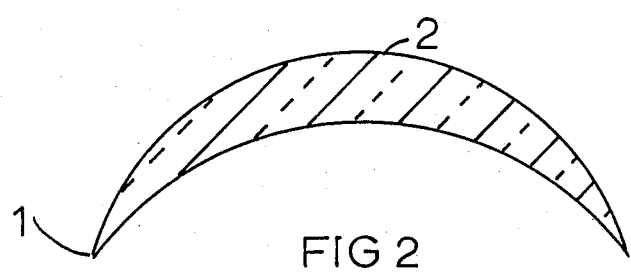
FIG. 2 shows a positive refractive lens in section.

Positive refractive power soft contact lenses FIG. 2 have a thin flexible edge 1 FIG. 2 and a thick less flexible center 2 FIG. 2. These configurations are required to provide the negative refractive power required for the correction of myopia and the positive refractive power required for the correction of hyperopia.

The present corneal drug delivery invention is not a lens as it has a hole in the center to provide uncorrected vision through the hole. Our people refer to it as the doughnut.

Figure 3:
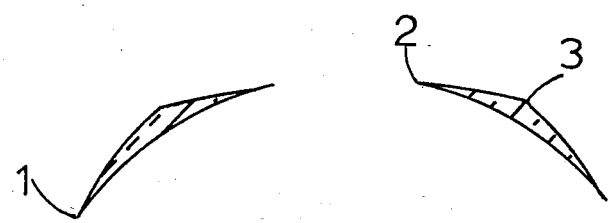
FIG. 3 shows the ocular drug delivery device in section.

It has been found that if the central portion surrounding the hole has a minus configuration, the inner edge 2 FIG. 3 around the hole becomes flexible allowing the central edge to flex and assume the shape of the cornea. A minus configuration would result in a thick edge 1 FIG. 1 which cannot conform to the edge of the cornea. No optics are required of the drug delivery device therefore the outer portion is made with a plus configuration having a thin outer edge 1 FIG. 3 that assumes the shape of the peripheral area of the cornea. The mid-point or area between the central minus edge and the peripheral plus edge 3 FIG. 3 remains thick to provide stability and ease of handling.

The aperture drug delivery device has two edges, an outer peripheral edge and an inner edge surrounding the central visual aperture. When the drug delivery device is placed on a cornea having a longer radius of curvature than the concave surface of the device force is exerted against the outer edge 1 FIG. 3 moving the edge toward a longer concave radius. Movement of the outer edge 1 FIG. 3 will result in a movement of the inner edge 2 FIG. 3 toward the cornea providing the longer radius needed to fit the corneal curvature. The thick mid-point 3 FIG. 3 becomes the fulcrum between the inner edge 2 FIG. 3 and the outer edge 1 FIG. 3. The outer edge moves outward to assume a longer radius and the inner edge moves inward to also assume the longer corneal radius. When placed on a steeper cornea the reverse movements occur allowing the cosmetic device to conform to the steep corneal curvature. Capillary attraction between the wet concave device surface and the wet convex corneal surface holds the device in place. The action of the eyelids also contribute to lens positioning.

Figure 4:
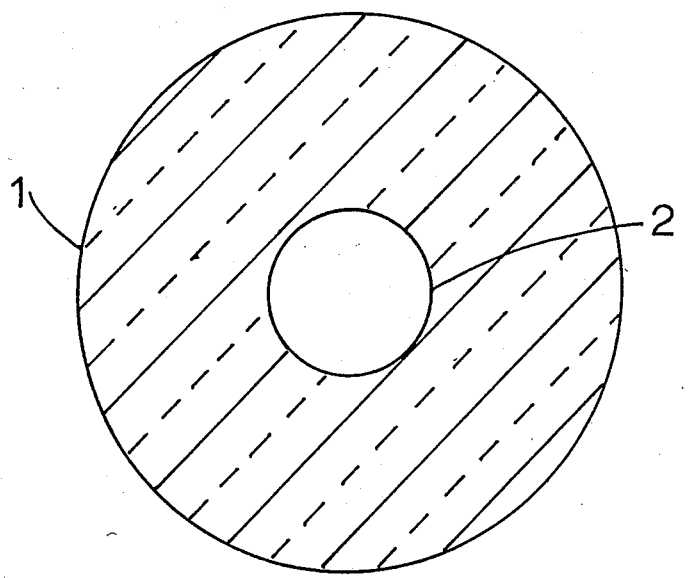
FIG. 4 shows the ocular drug delivery device from the front.

The device having a flexible central area 2 FIG. 4 and a flexible peripheral area 1 FIG. 4 has a wide fitting latitude. The central area 2 FIG. 3 and the peripheral area 1 FIG. 3 conform to the cornea shapes either steeper or flatter than the curvature present on the concave surface of the drug delivery device. This feature makes it possible for one drug delivery device to fit many different corneal shapes.

Aperture drug delivery devices provide no refractive correction. Persons requiring refractive corrections must wear eye glasses over the device.

It should be understood that the invention is not limited to the exact details of construction shown and described herein for obvious modifications will occur to persons skilled in the art.

I claim:

1. A non-optical corneal drug delivery device that releases a drug contained in the corneal drug delivery device at a predetermined rate and is substantially the size and curvature of the cornea upon which it is placed and has a central visual aperture substantially the size of the pupil and positioned on the cornea around the pupil of the eye, the convex surface is tapered to form a thin flexible outer peripheral edge, the convex surface is also tapered to form a thin flexible inner edge surrounding the central pupil aperture, whereby both the inner central pupil aperture edge and the outer peripheral edge are flexible and conform to the shape of the cornea on which the corneal drug delivery device is applied.

2. A non-optical ocular device that releases a medication to the eye at a controlled rate and is substantially the size and curvature of the cornea and has a central non-optical visual aperture substantially the size of the pupil and is positioned on the cornea surrounding the pupil of the eye, the convex surface of the device is shaped to form a thin and flexible outer peripheral edge, the convex surface of the device is also shaped to form a thin and flexible inner edge surrounding the central pupil aperture, whereby both the inner pupil aperture edge and the outer peripheral edge are flexible and conform to the shape of the cornea on which the medication delivery device is applied.

3. An ocular drug delivery device substantially the size and curvature of the cornea having a central visual aperture substantially the size of the pupil and positioned on the cornea to surround the pupil, the convex surface shape forms a thin, flexible outer peripheral edge, the convex surface shape also forms a thin, flexible inner edge surrounding the central pupil aperture, whereby both the inner pupil aperture edge and the outer peripheral edge are flexible and are allowed to conform to the shape of the cornea and the drug contained in the ocular drug delivery device is released to the eye at a predetermined rate.

4. The subject matter set forth in claim 1 wherein a colored dye is applied to the device.

5. The subject matter set forth in claim 2 wherein a colored dye is applied to the device.

6. The subject matter set forth in claim 3 wherein a colored dye is applied to the device.

7. The subject matter set forth in claim 1 wherein a colorant is added to the liquid monomer before the liquid monomer is polymerized to form the device.

8. The subject matter set forth in claim 2 wherein a colorant is added to the liquid monomer before the liquid monomer is polymerized to form the device.

9. The subject matter set forth in claim 3 wherein a colorant is added to the liquid monomer before the liquid monomer is polymerized to form the device.

10. The subject matter set forth in claim 1 wherein the device is made from a translucent material.

11. The subject matter set forth in claim 2 wherein the device is made from a translucent material.

12. The subject matter set forth in claim 3 wherein the device is made from a translucent material.

13. The subject matter set forth in claim 1 wherein a desirable medication is contained in the device material and released to the eye at a predetermined rate.

14. The subject matter set forth in claim 2 wherein a desirable drug is contained in the device material and released to the eye at a predetermined rate.

15. The subject matter set forth in claim 3 wherein a desirable medication is contained in the device material and released to the eye at a predetermined rate.

16. The subject matter set forth in claim 1 wherein antimicrobial agents are added to the device material.

17. The subject matter set forth in claim 2 wherein antimicrobial agents are added to the device material.

18. The subject matter set forth in claim 3 wherein antimicrobial agents are added to the device material.

19. The subject matter set forth in claim 1 wherein the ocular drug delivery device will conform to the shape of a cornea having a radius of curvature longer than the radius present on the concave surface of the ocular device.

20. The subject matter set forth in claim 1 wherein the ocular drug delivery device will conform to the shape of a cornea having a radius of curvature shorter than the radius present on the concave surface of the ocular device.

21. The subject matter set forth in claim 2 wherein the ocular medication delivery device will conform to the shape of a cornea having a radius of curvature longer than the radius present on the concave surface of the ocular device.

22. The subject matter set forth in claim 2 wherein the ocular medication delivery device will conform to the shape of a cornea having a radius of curvature shorter than the radius present on the concave surface of the ocular device.

23. The subject matter set forth in claim 3 wherein the ocular drug delivery device will conform to the shape of a cornea having a radius of curvature longer than the radius present on the concave surface of the ocular device.

24. The subject matter set forth in claim 3 wherein the ocular drug delivery device will conform to the shape of a cornea having a radius of curvature shorter than the radius present on the concave surface of the ocular device.

25. A non-optical corneal drug delivery device that releases a drug contained in the corneal drug delivery device at a predetermined rate and has a diameter of from 10.0 milimeters to 16.0 milimeters and has a concave radius of from 5.43 milimeters to 9.85 milimeters and has a central visual aperture having a diameter of from 4.0 milimeters to 7.0 milimeters and is positioned on the cornea around the pupil of the eye, the convex surface is tapered to form a thin flexible outer peripheral edge, the convex surface is also tapered to form a thin flexible inner edge surrounding the central pupil aperture, whereby both the inner central pupil aperture edge and the outer peripheral edge are flexible and conform to the shape of the cornea on which the corneal drug delivery device is applied.

* * * * *